US006630415B2

(12) United States Patent  
Phillips et al.

(10) Patent No.: US 6,630,415 B2
(45) Date of Patent: Oct. 7, 2003

(54) DURABLE HYDROPHILIC COATING FOR TEXTILES

(75) Inventors: Christine J. Phillips, Slingerlands, NY (US); Susan A. Nye, Feura Bush, NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/997,939

(22) Filed: Nov. 29, 2001

(65) Prior Publication Data

US 2002/0061406 A1 May 23, 2002

Related U.S. Application Data

(63) Continuation-in-part of application No. 09/443,182, filed on Nov. 19, 1999, now abandoned, which is a continuation of application No. 08/995,389, filed on Dec. 22, 1997, now abandoned.

(51) Int. Cl.$^7$ ............................................... B32B 27/08
(52) U.S. Cl. ...................... 442/119; 428/447; 428/445; 556/445
(58) Field of Search ........................... 442/119; 556/445

(56) References Cited

U.S. PATENT DOCUMENTS

| | | |
|---|---|---|
| 2,803,619 A | 8/1957 | Dickmann |
| RE25,727 E | 2/1965 | Haluska |
| 3,271,331 A | 9/1966 | Ender |
| 3,654,215 A | 4/1972 | Goossens |
| 3,817,910 A | 6/1974 | Vikmer |
| 3,984,200 A | 10/1976 | Doesburg |
| 4,097,943 A | 7/1978 | O'Connell |
| 4,105,567 A | 8/1978 | Koerner et al. |
| 4,287,261 A | 9/1981 | West et al. |
| 4,351,871 A | 9/1982 | Lewis et al. |
| 4,369,231 A | 1/1983 | West et al. |
| 4,376,149 A | 3/1983 | Martin |
| 4,539,357 A | 9/1985 | Bobear |
| 4,552,671 A | 11/1985 | Ogiso et al. |
| 4,554,147 A | 11/1985 | Stoll et al. |
| 4,690,967 A | 9/1987 | LaGarde et al. |
| 4,740,528 A | 4/1988 | Garvey et al. |
| 4,818,421 A | 4/1989 | Boris et al. |
| 4,857,251 A | 8/1989 | Nohr et al. |
| 4,921,622 A | 5/1990 | Kato et al. |
| 5,004,643 A | 4/1991 | Caldwell |
| 5,010,883 A | 4/1991 | Rawlings et al. |
| 5,045,387 A | 9/1991 | Schmalz |
| 5,051,259 A | 9/1991 | Olsen et al. |
| 5,057,361 A | 10/1991 | Sayovitz et al. |
| 5,081,172 A | 1/1992 | Chaffee et al. |
| 5,104,919 A | 4/1992 | Okami et al. |
| 5,110,845 A | 5/1992 | Gray et al. |
| 5,112,885 A | 5/1992 | Inoue et al. |
| 5,122,562 A | 6/1992 | Jeram et al. |
| 5,132,047 A | 7/1992 | Tanaka et al. |
| 5,153,244 A | 10/1992 | Akitomo et al. |
| 5,183,702 A | 2/1993 | Taylor et al. |
| 5,200,440 A | 4/1993 | Takago et al. |
| 5,209,965 A | 5/1993 | Caldwell |
| 5,210,133 A | 5/1993 | O'Lenick, Jr. |
| 5,219,922 A | 6/1993 | Steinberger et al. |
| 5,236,532 A | 8/1993 | Taylor et al. |
| 5,248,715 A | 9/1993 | Gray et al. |
| 5,258,129 A | 11/1993 | Kato et al. |
| 5,260,364 A | 11/1993 | Johnson |
| 5,276,123 A | 1/1994 | King et al. |
| 5,283,023 A | 2/1994 | Nohr et al. |
| 5,380,260 A | 1/1995 | Blott |
| 5,380,770 A | 1/1995 | Doin et al. |
| 5,418,051 A | 5/1995 | Caldwell |
| 5,447,783 A | 9/1995 | Horn |
| 5,474,839 A | 12/1995 | Ogawa et al. |
| 5,486,551 A | 1/1996 | Polmanteer |
| 5,500,254 A | 3/1996 | Quincy, III et al. |
| 5,519,082 A | 5/1996 | Yoshino |
| 5,540,984 A | 7/1996 | Quincy, III et al. |
| 5,556,919 A | 9/1996 | Oyama et al. |
| 5,569,688 A | 10/1996 | Meguriya et al. |
| 5,597,853 A | 1/1997 | Itoh et al. |
| 5,607,992 A | 3/1997 | Chiba et al. |
| 5,610,213 A | 3/1997 | Sumpter et al. |
| 5,620,788 A | 4/1997 | Garavaglia et al. |
| 5,623,028 A | 4/1997 | Fitzgerald et al. |
| 5,633,007 A | 5/1997 | Webb et al. |
| 5,698,303 A | 12/1997 | Caldwell |
| 5,811,482 A * | 9/1998 | Sabia et al. ................. 524/366 |
| 6,103,847 A * | 8/2000 | Lewis et al. .................. 528/21 |

FOREIGN PATENT DOCUMENTS

| | | |
|---|---|---|
| EP | 0 622 421 A2 | 11/1994 |
| EP | 0 671 500 A2 | 9/1995 |
| GB | 1 039 871 | 8/1966 |
| GB | 2 056 995 | 3/1981 |
| JP | 56041263 | 4/1981 |

* cited by examiner

*Primary Examiner*—Margaret G. Moore
(74) *Attorney, Agent, or Firm*—Kenneth S. Wheelock

(57) ABSTRACT

Low molecular weight silicone polyether ABA type block copolymer treatments wherein a linear polysiloxane is terminated at each end by a polyether moiety derived from ethylene oxide are useful to imparting a hydrophilic coating to the surface of either woven or non-woven textiles.

10 Claims, No Drawings

DURABLE HYDROPHILIC COATING FOR TEXTILES

CROSS-REFERENCE TO RELATED APPLICATIONS

This application is a continuation-in-part application of U.S. Ser. No. 09/443,182 filed Nov. 19, 1999, now abandoned, which is a continuation of U.S. Ser. No. 08/995,389 filed Dec. 22, 1997, now abandoned.

FIELD OF THE INVENTION

The present invention relates to low molecular weight silicone polyether ABA type block copolymers that are useful to imparting a hydrophilic coating to the surface of either woven or non-woven textiles.

BACKGROUND OF THE INVENTION

Textiles are made from a variety of materials both natural and man made. Natural textiles include cotton, wool, silk, linen and the like while synthetic textiles are derived from various high polymers such as polyesters, polyamides, polyimides, and the various polyolefins, e.g. polyethylene, polypropylene, polybutylene. While polymers are used extensively to make a variety of products ranging from blown and cast films, extruded sheets, injection molded articles, foams, blow molded articles, extruded pipe, monofilaments and non-woven webs many of the polymers used for such materials are hydrophobic. In many cases this property is an advantage.

There are a number of uses to which polymers may be put where their hydrophobic nature either limits their usefulness or requires some modification. This is particularly true of polyolefins such as polyethylene and polypropylene which are used to manufacture polymeric fabrics which are used in disposable absorbent articles such as diapers, training pants, incontinence products, wipes, feminine care products and the like. These polymeric fabrics are typically non-woven webs prepared by meltblowing, coforming or spunbonding. For uses such as the foregoing these non-woven fabrics need to be wettable. Frequently wettability can be obtained by coating the fabric in some fashion with a treatment solution during or after formation of the fabric web and drying the web.

Some of the more commonly applied topically applied treatments are nonionic treatments, for example polyethoxylated octylphenols and the condensation products of propylene oxide with propylene glycol. These types of treatments are effective in rendering normally hydrophobic polymeric fabrics wettable or hydrophilic. However, the treatment is readily removed from the fabric, often after only a single exposure to an aqueous liquid.

There have been several different approaches to increasing the durability of treatments that are topically applied to the surface of a fabric. Among these approaches have been:

(1) the use of a composition that includes water, a primary treatment, and a co-treatment that functions to wet the fabric with the treatment composition and that provides for a substantially uniform distribution of the primary treatment onto the fabric;

(2) the use of a treatment, with or without a nonionic co-treatment that is the reaction product of an acid anhydride derivative with a polyhydroxy compound, polyethylene glycol, triethanolamine, a polyhydroxyamine, and certain unsaturated aliphatic sulfo compounds;

(3) the use of a treatment, with or without a nonionic co-treatment that is the reaction product of certain unsaturated aliphatic sulfo compounds with the reaction product of an acid anhydride derivative with a polyamine having at least one NH group capable of addition to a double bond;

(4) the use of a treatment mixture that includes an ester acid, ester salt, or a mixture thereof, and an amide-acid, amide-salt or mixture thereof with or without a nonionic co-treatment;

(5) the use of a treatment mixture that includes a sorbitol succinate treatment and a co-wetting aid that can be a silicone polyether or a primary or secondary alcohol; and (6) the use of a silicone polyether treatment having the formula:

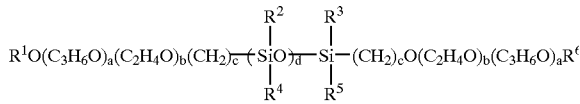

where $R^1$ and $R^6$ are selected from the group of hydrogen and $C_{1-8}$ alkyl and aryl, $R^2, R^3, R^4$ and $R^5$ are selected from the group of $C_{1-8}$ alkyl and aryl, the subscript a represents an integer ranging from about 8 to about 25, the subscript b represents an integer ranging from about 8 to about 25, the ratio of b to a is in a range of from about 0.7 to about 1.5, the subscript c represents an integer from 1 to about 10, the subscript d represents an integer of from about 40 to about 70 the ratio of d to two times the sum of a and b is in a range of from about 0.7 to about 1.5 and the number average molecular weight is preferably in a range of from about 5,000 to about 35,000, more preferably from about 6,500 to about 18,500 and most preferably about 7,000.

The examples of U.S. Pat. No. 5,540,984 ('984) teach that silicone polyether treatments having a molecular weight below about 7,000 do not provide the durability provided by patentee's invention. Further, the polyether endgroups on the silicone treatments employed by the '984 patent ranged from about 50 to 80 weight percent propylene oxide and from about 50 to about 20 weight percent ethylene oxide. The '984 patent specifically teaches that reversing this weight ratio of polyether end groups to 85 weight percent ethylene oxide and 15 weight percent propylene oxide (patentee's example P) does not provide a durable hydrophilic coating as defined by patentee. This is emphasized by patentee's results for a silicone polyether treatment having 100 weight per cent ethylene oxide polyether groups wherein the treatment was not durable (patentee's example J). Thus, the '984 patent teaches that the polyether substituents of the silicone polyether treatment must contain a mix of ethylene oxide and propylene oxide groups or preferably all propylene oxide groups. These results were obtained for copolymers terminated with the respective polyether moieties.

Notwithstanding the advances that have been made in rendering fabrics wettable by providing for a hydrophilic coating there remains a need for further improvement in these areas.

SUMMARY OF THE INVENTION

The present invention provides for a treatment silicone compound selected from the group consisting of:

1) polysiloxane polyethers having the formula:

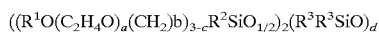

where $R^1$ is selected from the group consisting of hydrogen and alkyls and $R^2$ and $R^3$ are each independently selected from the group consisting of one to forty carbon atom monovalent hydrocarbon radicals; the subscript a ranges from about 1 to about 8; the subscript b ranges from about 1 to about 10; the subscript c ranges from zero to 2; the subscript d ranges from about to 1 to about 10; and the number average molecular weight ranging from ranges from about to 300 to about 1,000.

2) polysiloxane polyethers having the formula:

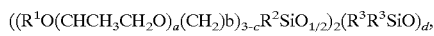

where $R^1$ is selected from the group consisting of hydrogen and alkyls and $R^2$ and $R^3$ are each independently selected from the group consisting of one to forty carbon atom monovalent hydrocarbon radicals; the subscript a ranges from about to 1 to about 8; the subscript b ranges from about 1 to about 10; the subscript c ranges from zero to 2; the subscript d ranges from about to 1 to about 10; and the number average molecular weight ranging from ranges from about to 300 to about 1,000;

3) polysiloxane polyethers having the formula:

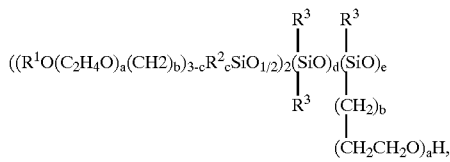

where $R^1$ is selected from the group consisting of hydrogen and alkyls and $R^2$ and $R^3$ are each independently selected from the group consisting of one to forty carbon atom monovalent hydrocarbon radicals; the subscript a ranges from about to 1 to about 8; the subscript b ranges from about 1 to about 10; the subscript c ranges from zero to 2; the subscript d ranges from about to 1 to about 10; the subscript e ranges from about to 1 to about 10; and the number average molecular weight ranging from ranges from about to 300 to about 1,000; and 5) mixtures thereof.

Such treatment silicone compositions are useful for treating fabrics comprised of natural or synthetic polymeric materials to render the fabrics hydrophilic, i.e. capable of picking up and absorbing quantities of water. Such treatment silicone compositions are useful for treating cellulosic materials such as paper.

DETAILED DESCRIPTION OF THE INVENTION

As used herein, the term "polymeric fabric" means a fabric prepared from any polymeric material capable of being formed into a fabric and includes fabric webs such as paper. Thus, such material can be synthetic or natural, although the former are more likely to be employed in the present invention. Examples of natural polymeric materials include, cotton, silk, wool, and cellulose, by way of illustration only. Synthetic polymeric materials, in turn, can be either thermosetting or thermoplastic materials, with thermoplastic materials being more common. As used herein fabric means any textile, non-woven or woven, or any web such as paper or felt.

Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novalacs and resols; and thermosetting polyesters, silicones, and urethanes.

Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly( epsilon-caprolactam), poly(hexamethylene adipamide), poly(hexamethylene sebacamide), poly(11-amino-undecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxyl-1,4-phenylenesulfonyl-4,4'-biphenylene), and the like; polycarbonates, such as poly(bisphenolA)orpoly(carbonyldioxy-1,4-phenyleneisopropylidene-1,4-phenylene), and the like; polyesters, such as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like: copolymers of the foregoing, such as acrylonitrile-butadiene-styrene (ABS) copolymers, and the like; and the like. In certain embodiments, the polymeric fabric will be prepared from a polyolefin. In other embodiments, the polyolefin will be polypropylene or polyethylene.

The term "fabric" is used broadly herein to mean any fibrous material which has been formed into a sheet or web. That is, the fabric is composed, at least in part, of fibers of any length. Thus, the fabric can be a woven or nonwoven sheet or web, all of which are readily prepared by methods well-known to those having ordinary skill in the art. For example, nonwoven webs are prepared by such processes as meltblowing, coforming, spunbonding, carding, air laying, and wet laying. Moreover, the fabric can consist of a single layer or multiple layers. In addition, a multilayered fabric can include films, scrim, and other nonfibrous materials.

As used herein, the term "durable" means that the polymeric fabric to which a treatment has been applied can be subjected to the rigorous washing procedure described hereinafter or to multiple exposures to water and remain wettable.

The term "treatment" is used herein to mean any active agent that is capable of durably rendering a polymeric fabric (i.e. a fabric either woven or non-woven made from a polymeric fiber) wettable. In some embodiments, the treatment is a linear polysiloxane that is terminated at each end by a polyether moiety derived from ethylene oxide, commonly referred to as an A-B-A polymer. In one embodiment, the treatment is a polysiloxane polyether having the general formula:

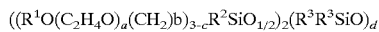

where $R^1$ is selected from the group consisting of hydrogen and alkyls and $R^2$ and $R^3$ are each independently selected from the group consisting of one to forty carbon atom monovalent hydrocarbon radicals; the subscript a ranges from about to 1 to about 8, preferably from about to 1.5 to about 6, more preferably from about to 1.5 to about 5, and most preferably from about to 1.5 to about 4; the subscript b ranges from about 1 to about 10, preferably from about 1 to about 7, more preferably from about 1 to about 5, and most preferably from about to 1 to about 3; the subscript c ranges from zero to 2, more preferably from 1 to 2, and is most preferably 2; the subscript d ranges from about to 1 to about 10, preferably from about to 2 to about 8, more preferably from about to 2 to about 7, and most preferably from about to 3 to about 5; and the number average molecular weight ranging from ranges from about to 300 to about 1,000, preferably from about to 400 to about 900 ,more preferably from about to 500 to about 900, and most preferably from about to 600 to about 800.

In a second embodiment, the treatment is a polysiloxane polyether having the general formula:

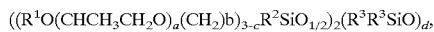

where $R^1$ is selected from the group consisting of hydrogen and alkyls and $R^2$ and $R^3$ are each independently selected from the group consisting of one to forty carbon atom monovalent hydrocarbon radicals; the subscript a ranges from about to 1 to about 8, preferably from about to 1.5 to about 6 ,more preferably from about to 1.5 to about 5, and most preferably from about to 1.5 to about 4; the subscript b ranges from about 1 to about 10, preferably from about 1 to about 7, more preferably from about 1 to about 5, and most preferably from about to 1 to about 3; the subscript c ranges from zero to 2, more preferably from 1 to 2, and is most preferably 2; the subscript d ranges from about to 1 to about 10, preferably from about to 2 to about 8, more preferably from about to 2 to about 7, and most preferably from about to 3 to about 5; and the number average molecular weight ranging from ranges from about to 300 to about 1,000, preferably from about to 400 to about 900, more preferably from about to 500 to about 900, and most preferably from about to 600 to about 800.

In a third embodiment, the treatment is a polysiloxane polyether having the general formula:

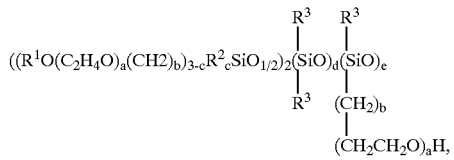

where $R^1$ is selected from the group consisting of hydrogen and alkyls and $R^2$ and $R^3$ are each independently selected from the group consisting of one to forty carbon atom monovalent hydrocarbon radicals; the subscript a ranges from about to 1 to about 8, preferably from about to 1.5 to about 6, more preferably from about to 1.5 to about 5, and most preferably from about to 1.5 to about 4; the subscript b ranges from about 1 to about 10, preferably from about 1 to about 7, more preferably from about 1 to about 5, and most preferably from about to 1 to about 3 ; the subscript c ranges from zero to 2, more preferably from 1 to 2, and is most preferably 2; the subscript d ranges from about to 1 to about 10, preferably from about to 2 to about 8, more preferably from about to 2 to about 7, and most preferably from about to 3 to about 5; the subscript e ranges from about to 1 to about 10, preferably from about to 2 to about 8, more preferably from about to 2 to about 7, and most preferably from about to 3 to about 5; and the number average molecular weight ranging from ranges from about to 300 to about 1,000, preferably from about to 400 to about 900, more preferably from about to 500 to about 900, and most preferably from about to 600 to about 800.

In a fourth embodiment the treatment of the present invention is a mixture comprising two or more of the first, second and third embodiments. It should be noted that for molecular species the subscripts a, b, c, d etc. will assume integral values. When a mixture of compounds is employed as the treatment component, the values of the subscripts will assume non-integral values depending on the population fraction for a given molecular weight, i.e. molar averaged stoichiometric subscripts will be non-integral in the case of mixtures as opposed to pure compounds.

The advantages of the present invention are that the silicone polyether compounds of the present invention do not require a co-treatment. The materials also are effective at extremely low levels and maintain effectiveness after as many as five washings. Thus the materials maintain effectiveness after one, two, three, four and five washings. Effectiveness as to the hydrophilic coating is defined in the experimental section.

The hydrophilic coatings or treatments of the present invention typically comprise from about 0.01 to about 20.00 weight percent of the total weight of the treated fabric, preferably from about 0.10 to about 10.00 weight percent of the total weight of the treated fabric, more preferably from about 0.50 to about 5.00 weight percent of the total weight of the treated fabric, and most preferably from about 0.75 to about 2.50weight percent of the total weight of the treated fabric.

Depending on the means employed to coat the fabric, the coated fabric may demonstrate a greater or lesser hydrophilic behavior for a given treatment composition depending on whether the coating is applied from an aqueous solution or dispersion or an alcoholic solution or dispersion. The greatest hydrophilic behavior is observed when the hydrophilic coating is applied from an aqueous dispersion, particularly when water is the only solvent employed. Textiles treated by the treatment of the present invention are useful for disposable absorbent articles such as diapers, training pants, incontinence products, wipes, feminine care products and the like. Wipes may be personal care wipes, floor care wipes, household care wipes, automotive care wipes and the like. In one embodiment, the treatment of the present invention, heretofore referred to as a coating, which coating may be a partial coating or a complete coating, involves depositing the treating agent, the compounds used in the present invention, onto the textile or fabric being treated to render it hydrophilic, preferably durably hydrophilic.

All U.S. patents referenced herein are specifically herewith and hereby incorporated by reference.

The following experiments are to be regarded as illustrative only and are not intended by their presentation to constitute any limitations upon the appended claims.

EXPERIMENTAL

The base fabric used in evaluating the coating compositions of the present invention was a spunbound polypropylene nonwoven web having a basis weight of 15.5 g per square meter. The fabric was cut into test swatches having dimensions of 22±5 cm ×28±5 cm and an average weight ranging from 0.9 to 1.1 g (1.00±0.10 g). The silicone polyether compounds evaluated had the following structural formulas:

structure type A:

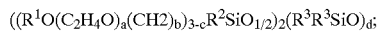
$$((R^1O(C_2H_4O)_a(CH2)_b)_{3-c}R^2SiO_{1/2})_2(R^3R^3SiO)_d;$$

structure type B:

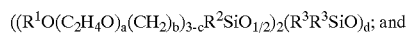
$$((R^1O(C_2H_4O)_a(CH2)_b)_{3-c}R^2SiO_{1/2})_2(R^3R^3SiO)_d; \text{ and}$$

structure type C:

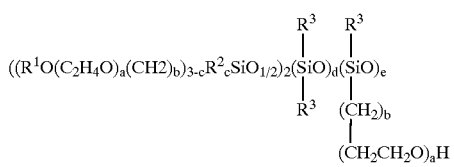
$$((R^1O(C_2H_4O)_a(CH2)_b)_{3-c}R^2_cSiO_{1/2})_2(\underset{\underset{R^3}{|}}{\overset{\overset{R^3}{|}}{Si}}O)_d(\underset{\underset{(CH_2)_b}{|}}{\overset{\overset{R^3}{|}}{Si}}O)_e$$
$$(CH_2CH_2O)_aH$$

The silicone polyether compounds evaluated for the purposes of the present invention are listed in Table 1.

TABLE 1

Structural Parameters for Silicone Polyethers

| Sample No. | Type | $R^1$ | $R^2$ | $R^3$ | a | b | c | d | e |
|---|---|---|---|---|---|---|---|---|---|
| 1 | A | H | $CH_3$ | $CH_3$ | 1.8 | 3 | 2 | 3 | 0 |
| 2 | A | H | $CH_3$ | $CH_3$ | 4 | 3 | 2 | 0 | 0 |
| 3 | A | H | $CH_3$ | $CH_3$ | 4 | 3 | 2 | 3 | 0 |
| 4 | A | H | $CH_3$ | $CH_3$ | 4 | 3 | 2 | 4 | 0 |
| 5 | A | H | $CH_3$ | $CH_3$ | 4 | 3 | 2 | 5 | 0 |
| 6 | A | H | $CH_3$ | $CH_3$ | 8 | 3 | 2 | 3 | 0 |
| 7 | A | H | $CH_3$ | $CH_3$ | 8 | 3 | 2 | 5 | 0 |
| 8 | A | H | $CH_3$ | $CH_3$ | 8 | 3 | 2 | 10 | 0 |
| 9 | A | H | $CH_3$ | $CH_3$ | 12 | 3 | 2 | 15 | 0 |
| 10 | A | H | $CH_3$ | $CH_3$ | 20 | 3 | 2 | 25 | 0 |
| 11 | B | H | $CH_3$ | $CH_3$ | 1.7 | 3 | 2 | 3 | 0 |
| 12 | C | H | $CH_3$ | $CH_3$ | 12 | 3 | 3 | 20 | 3 |

The silicone polyethers listed in Table 1 were suspended or dissolved in a 50 weight percent aqueous solution of isopropanol (2-propanol) or water at levels of 2.0, 0.5, 0.4 and 0.1 weight percent. Samples of the nonwoven spunbonded polypropylene fabric were treated by soaking them in the water-alcohol-silicone polyether mixture for 1–2 hours followed by drying in a forced air oven for 30 minutes at 105° C. The treated fabrics, having swatch dimensions of 22×28 cm. and weighing on average 0.95 g each were tested for hydrophilicity by pouring 100 g of water onto the fabric samples while the fabric sample was supported at a 35° angle above horizontal with an absorbent pad directly underneath the sample, which is known in the art as a run-off test. The absorbent pad was obtained by placing ten layers of commercially available paper towels one on top of each other; the paper towels having essentially the same dimensions as the fabric test swatch. Any of the water that ran off the fabric and was not absorbed was collected and measured. The treated fabric was judged effective or as having an effective hydrophilic coating if the fabric swatch and the absorbent pad thereunder retained 80 g of the 100 g poured onto the fabric, i.e. 80%. Conversely, if 20 g of water or more was recovered from the test the fabric sample was deemed to have failed the test. Fabrics that were treated with a water solution or dispersion of the compounds of the present invention tended to perform better than fabrics treated with alcoholic solutions or dispersions. The amount of coating it is possible to impart to the treated fabric tends to be a function of how the fabric is treated, i.e. whether the external surfaces of the fabric are treated or whether the entire fabric is immersed into the impregnating solution or dispersion.

TABLE 2

Coating Weights of Hydrophilic Silicone Coating on Textile Samples

| Sample No. | A | D | Solution Concentration of Silicone, wt. % | Concentration of Aqueous iso-Pr-OH | Coating Weight of Silicone, wt. % |
|---|---|---|---|---|---|
| A-1 | 1.8 | 3 | 0.05 | 0 | 4.67 |
| A-3 | 4 | 3 | 2.00 | 50 | 6.59 |
| A-3 | 4 | 3 | 0.50 | 50 | 0.66 |
| A-3 | 4 | 3 | 0.40 | 50 | 1.20 |
| A-3 | 4 | 3 | 0.40 | 0 | 15.03 |
| A-3 | 4 | 3 | 0.30 | 0 | 6.88 |
| A-3 | 4 | 3 | 0.20 | 0 | 4.64 |
| A-3 | 4 | 3 | 0.10 | 0 | 1.75 |
| A-3 | 4 | 3 | 0.05 | 0 | 1.68 |
| A-5 | 4 | 5 | 2.00 | 50 | 8.01 |
| A-5 | 4 | 5 | 0.50 | 50 | 1.30 |
| A-5 | 4 | 5 | 0.05 | 0 | 1.25 |
| A-6 | 8 | 3 | 0.05 | 0 | 0 |
| A-7 | 8 | 5 | 2.00 | 50 | 3.44 |
| A-8 | 8 | 10 | 2.00 | 50 | 3.78 |
| A-8 | 8 | 10 | 0.05 | 28 | 0 |
| A-9 | 12 | 15 | 0.05 | 28 | 0 |

TABLE 2-continued

Coating Weights of Hydrophilic Silicone Coating on Textile Samples

| Sample No. | A | D | Solution Concentration of Silicone, wt. % | Concentration of Aqueous iso-Pr-OH | Coating Weight of Silicone, wt. % |
|---|---|---|---|---|---|
| A-10 | 20 | 25 | 0.05 | 28 | 0.02 |
| B-1  | 1.7 | 2 | 2.00 | 50 | 9.01 |
| B-1  | 1.7 | 3 | 0.50 | 50 | 1.31 |
| C-1  | 8 | 1 | 0.05 | 0 | 0 |
| C-2  | 12 | 3 | 2.00 | 50 | 5.39 |
| C-2  | 12 | 3 | 0.05 | 28 | 0.05 |

The coated textiles when coated with the compounds of the present invention will pick up varying amounts of water depending on how extensively the textile is treated. If only the external surfaces of the textile are treated at very low levels, the total amount of water absorbed by the treated textile will be very low and may be indistinguishable from an untreated fabric. However, if the entire body of the fabric, exterior and interior, has been treated, the treated fabric can absorb as much as 300 to 400 weight percent.

Having described the invention that which is claimed is:

1. A polymeric fabric treated with a silicone compound selected from the group consisting of:

1) polysiloxane polyethers having the formula:

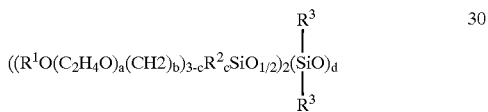

where $R^1$ is selected from the group consisting of hydrogen and alkyls and $R^2$ and $R^3$ are each independently selected from the group consisting of one to forty carbon atom monovalent alkyl radicals; the subscript a ranges from about 1 to about 8; the subscript b ranges from about 1 to about 10; the subscript c ranges from zero to 2; the subscript d ranges from about to 1 to about 10; and the number average molecular weight ranging from ranges from about to 300 to about 1,000, whereby said fabric is rendered durably hydrophilic.

2. The polymeric fabric of claim 1 wherein said silicone is:

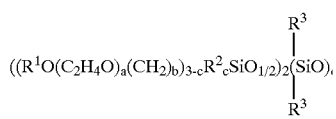

wherein the subscript d ranges from about 2 to about 8.

3. The polymeric fabric of claim 1 comprising a polymer wherein said polymer is selected from the group consisting of:

alkyd resins, ophthalmic anhydride-glycerol resins, maleic acid-glycerol resins, adipic acid-glycerol resins, phthalic anhydride-pentaerythritol resins; allylic resins cross-linked by diallyl phthalate, diallyl isophthalate diallyl maleate, or diallyl chlorendate; aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, epichlorohydrin-bisphenol A resins; phenolic resins, phenol-formaldehyde resins, end-capped polyacetals, poly(oxymethylene), polyformaldehyde, poly(trichloroacetaldehyde), poly(n-valeraldehyde), poly(acetaldehyde), poly(propionaldehyde), acrylic polymers, polyacrylamide, poly(acrylic acid), poly(methacrylic acid), poly(ethyl acrylate), poly(methyl methacrylate), fluorocarbon polymers, poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), polyamides, poly(6-aminocaproic acid), poly( epsilon -caprolactam), poly(hexamethylene adipamide), poly(hexamethylene sebacamide), poly(11-amino-undecanoic acid), polyaramides, poly(imino-1,3-phenyleneiminoisophthaloyl) or poly(m-phenylene isophthalamide), poly-p-xylylene, poly(chloro-p-xylylene), polyaryl ethers, poly(oxy-2,6-dimethyl-1,4-phenylene), poly(p-phenylene oxide), polyaryl sulfones, poly(oxy-1,4-phenylenesulfonyl-1,4-phenyleneoxy-1,4-phenylene-isopropylidene-1,4-phenylene), poly(sulfonyl-1,4-phenyleneoxy1,4-phenylensulfonyl-4,4'biphenylene), polycarbonates, poly(bisphenolA) or poly(carbonyldioxy-1,4-phenyleneisopropylidene-1,4-phenylene), polyesters, poly(ethylene terephthalate), poly(tetramethylene terephthalate), poly(cyclohexylene-1,4-dimethylene terephthalate), poly(oxymethylene-1,4-cyclohexylenemethyleneoxyterephthaloyl), polyaryl sulfides, poly(p-phenylene sulfide), poly(thio-1,4-phenylene), polyimides, poly(pyromellitimido-1,4-phenylene), polyolefins, polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, copolymers of the foregoing, acrylonitrile-butadiene-styrene (ABS) copolymers, and mixtures thereof.

4. The polymeric fabric of claim 3 wherein said polymer is selected from the group consisting of polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, copolymers of the foregoing, acrylonitrile-butadiene-styrene (ABS) copolymers, and mixtures thereof.

5. The polymeric fabric of claim 4 wherein said polymer is selected from the group consisting of polyethylene and polypropylene.

6. The polymeric fabric of claim 5 wherein said polymer is polyethylene.

7. The polymeric fabric of claim 6 wherein said polymer is polypropylene.

8. The polymeric fabric of claim 1 comprising a polymer wherein said polymer is a natural polymer selected from the group consisting of cotton, silk, wool, and cellulose.

9. The polymeric fabric of claim 8 wherein said polymer is cellulose.

10. The polymeric fabric of claim 9 wherein said cellulose is paper.

* * * * *